(12) United States Patent
Reeser et al.

(10) Patent No.: US 10,806,444 B2
(45) Date of Patent: Oct. 20, 2020

(54) MULTIPLE LEG SURGICAL FASTENER

(75) Inventors: Steven M. Reeser, Jacksonville, FL (US); Glen Jorgensen, Jacksonville, FL (US)

(73) Assignee: LAPROTX LLC, Jacksonville, FL (US)

( * ) Notice: Subject to any disclaimer, the term of this patent is extended or adjusted under 35 U.S.C. 154(b) by 0 days.

(21) Appl. No.: 13/604,114

(22) Filed: Sep. 5, 2012

(65) Prior Publication Data
US 2013/0331867 A1    Dec. 12, 2013

Related U.S. Application Data

(60) Provisional application No. 61/656,305, filed on Jun. 6, 2012.

(51) Int. Cl.
*A61B 17/064* (2006.01)
*A61B 17/04* (2006.01)

(52) U.S. Cl.
CPC .... *A61B 17/064* (2013.01); *A61B 2017/0427* (2013.01); *A61B 2017/0464* (2013.01); *A61B 2017/0641* (2013.01)

(58) Field of Classification Search
CPC .............. A61B 17/064; A61B 17/0644; A61B 2017/0427; A61B 2017/0464; A61B 2017/0645; A61B 2017/0412; A61B 2017/0437; A61B 2017/0401; A61B 17/0642; A61B 17/0643; A61B 17/122; A61B 17/1227; A61B 17/128; A61B 17/1285; A61B 2017/0641; A61B 2017/0646
USPC ........................................................ 606/151
See application file for complete search history.

(56) References Cited

U.S. PATENT DOCUMENTS

| 1,100,252 A | 6/1914 | O'Neil |
| RE27,725 E | 8/1973 | Brumlik |
| 3,757,629 A * | 9/1973 | Schneider ........... F16B 15/0015 227/83 |
| 4,612,933 A | 9/1986 | Brinkerhoff et al. |
| 4,976,715 A | 12/1990 | Bays et al. |

(Continued)

FOREIGN PATENT DOCUMENTS

| WO | WO 2007/097994 | 8/2007 |
| WO | WO 2012/015678 | 2/2012 |

OTHER PUBLICATIONS

International Search Report and the Written Opinion of the International Searching Authority for PCT/US2011/044927; dated Dec. 1, 2011.

*Primary Examiner* — Darwin P Erezo
*Assistant Examiner* — Christian D Knauss
(74) *Attorney, Agent, or Firm* — Pandiscio & Pandiscio

(57) ABSTRACT

A fastener is provided for inserting into a body tissue. The fastener has a head and an anchoring portion comprising a plurality of distally extending legs. Each leg terminates in an anchoring element configured to penetrate tissue and to cause a net lateral resistance force on the leg during penetration. The legs are configured and structured so that when the net lateral resistance force on the anchoring element exceeds a predetermined level, at least a portion of the leg is deflected laterally away from a pre-insertion configuration and so that when the net lateral force is subsequently reduced below the predetermined level, the at least a portion of the leg is biased back toward the pre-insertion configuration.

24 Claims, 16 Drawing Sheets

(56) References Cited

U.S. PATENT DOCUMENTS

| | | | |
|---|---|---|---|
| 4,994,073 A * | 2/1991 | Green | A61B 17/064 411/457 |
| 5,084,057 A | 1/1992 | Green et al. | |
| 5,333,624 A | 8/1994 | Tovey | |
| 5,557,898 A | 9/1996 | Dixon | |
| 5,728,116 A | 3/1998 | Rosenman | |
| 5,893,506 A | 4/1999 | Powell | |
| 5,941,890 A | 8/1999 | Voegele et al. | |
| 5,997,552 A | 12/1999 | Person et al. | |
| 6,099,552 A | 8/2000 | Adams | |
| 6,261,302 B1 | 7/2001 | Voegele et al. | |
| 6,346,109 B1 | 2/2002 | Fucci et al. | |
| 6,360,406 B1 * | 3/2002 | Patterson | H01R 13/6275 24/453 |
| 6,447,524 B1 | 9/2002 | Knodel et al. | |
| 7,758,612 B2 | 7/2010 | Shipp | |
| 7,815,652 B2 | 10/2010 | Messerly et al. | |
| 7,905,893 B2 | 3/2011 | Kuhns et al. | |
| 10,010,318 B2 | 7/2018 | Reeser | |
| 2002/0068947 A1 | 6/2002 | Kuhns et al. | |
| 2002/0087170 A1 | 7/2002 | Kuhns et al. | |
| 2002/0095163 A1 | 7/2002 | Beyar | |
| 2003/0021656 A1 * | 1/2003 | O'Banion | F16B 13/0816 411/477 |
| 2003/0088250 A1 * | 5/2003 | Colleran | A61B 17/0401 606/232 |
| 2004/0034357 A1 * | 2/2004 | Beane | A61L 31/16 606/232 |
| 2004/0122454 A1 * | 6/2004 | Wang | F04C 1/02 606/152 |
| 2004/0138705 A1 | 7/2004 | Heino et al. | |
| 2004/0138707 A1 * | 7/2004 | Greenhalgh | A61B 17/0401 606/232 |
| 2004/0161319 A1 | 8/2004 | O'Banion et al. | |
| 2005/0055027 A1 * | 3/2005 | Yeung | A61B 17/0401 606/75 |
| 2005/0192599 A1 | 9/2005 | Demarais | |
| 2005/0240222 A1 * | 10/2005 | Shipp | A61B 17/064 606/219 |
| 2006/0025785 A1 * | 2/2006 | Cully | A61F 2/0063 606/151 |
| 2006/0129154 A1 | 6/2006 | Shipp | |
| 2008/0077144 A1 | 3/2008 | Crofford | |
| 2008/0082177 A1 * | 4/2008 | Yang | A61F 2/0045 623/23.75 |
| 2008/0173691 A1 | 7/2008 | Mas et al. | |
| 2008/0217376 A1 | 9/2008 | Clauson et al. | |
| 2008/0228193 A1 | 9/2008 | Matityahu | |
| 2009/0030434 A1 * | 1/2009 | Paz | A61B 17/064 606/151 |
| 2010/0198192 A1 | 8/2010 | Serina et al. | |
| 2010/0292710 A1 | 11/2010 | Daniel et al. | |
| 2010/0292713 A1 | 11/2010 | Cohn et al. | |
| 2010/0292715 A1 * | 11/2010 | Nering | A61B 17/064 606/151 |
| 2012/0029538 A1 | 2/2012 | Reeser | |

* cited by examiner

MULTIPLE LEG SURGICAL FASTENER

This application claims priority to U.S. Provisional Application No. 61/656,305 filed Jun. 6, 2012, the complete disclosure of which is incorporated herein by reference in its entirety.

BACKGROUND OF THE INVENTION

The present invention relates generally to surgical fasteners and drive apparatus for use with surgical fasteners. More specifically, the present invention relates to multiple leg, soft tissue surgical tacks and apparatus and methods for applying such tacks.

Fasteners are used in various surgical procedures to secure tissue and objects to tissue. One such surgical procedure is the repair of a hernia. A common solution in hernia repair is to attach a mesh patch over the defect so that bowel and other abdominal tissue are blocked from forming an external bulge that is typical of abdominal hernias.

Various devices and fasteners are available to attach the mesh patch to the inguinal floor or abdominal wall. Such devices and fasteners include sutures, surgical staples, and tacks. The role of the devices and fasteners is to keep the mesh in proper position until tissue in-growth is adequate to hold the mesh in place under various internal and external conditions.

A hernia repair surgery can be performed either through the traditional open procedure or through the current trend of less invasive procedures such as laparoscopic procedures. Certain previously used devices and fasteners are better suited for open procedures while other devices and fasteners are better suited for laparoscopic procedures.

In either case, fasteners should be simple to deploy and securely fasten to bodily tissue. In addition, the ideal fastener would result in minimal tissue damage when inserted, but would exhibit high resistance to inadvertent withdrawal. In many cases (but not all), it may be advantageous that the fastener be absorbed by the body after a period of time when the tissue in-growth obviates the need for a fastener.

SUMMARY OF THE INVENTION

Aspects of the present invention provide a fastener for insertion into a body tissue. The fastener comprises a head having a proximal head surface and a distal head surface, at least a portion of the distal head surface being configured for bearing on a surface of the body tissue or a material to be attached to a surface of the body tissue. The head defines a longitudinal axis extending through the proximal and distal head surfaces. A leg base portion is attached to the distal head surface. The fastener further comprises a plurality of legs extending distally from the leg base portion. Each leg comprises a leg stem having a proximal end attached to the leg base portion and a distal end. Each leg also comprises an anchoring element attached to and extending distally from the distal end of the first leg stem. The anchoring element is configured for penetrating into the body tissue and for causing, while penetrating the body tissue, a net lateral resistance force in the body tissue acting on the anchoring element in a lateral direction relative to the longitudinal axis. The anchoring element and leg stem of each leg have a pre-insertion configuration and are structured and configured so that when the net lateral resistance force on the anchoring element exceeds a predetermined level, at least a portion of the leg is deflected in the direction of the net lateral resistance force acting on the anchoring element. The anchoring element and leg stem are also structured and configured so that when the net lateral force is reduced below the predetermined level, the at least a portion of the leg is biased back toward the pre-insertion configuration.

Aspects of the present invention provide a method of applying a fastener to a body tissue. The method comprises providing a fastener having a head and an anchoring portion comprising a plurality of distally extending legs. Each leg terminates in an anchoring element configured to penetrate tissue and to cause a net lateral resistance force on the leg during penetration. The legs are configured so that when the net lateral resistance force on the anchoring element exceeds a predetermined level, at least a portion of the leg is deflected laterally away from a pre-insertion configuration and so that when the net lateral force is subsequently reduced below the predetermined level, the at least a portion of the leg is biased back toward the pre-insertion configuration. The method further comprises positioning the fastener so that the anchoring element is adjacent a surface of the body tissue and imparting a longitudinal insertion force to the fastener. The insertion force is sufficient to cause the anchoring elements to penetrate the body tissue and to produce a net lateral force on each leg in excess of the predetermined level. This causes the at least a portion of each leg to deflect laterally within the body tissue. The method still further comprises removing the longitudinal insertion force so as to allow the anchoring element to stop penetrating the body tissue, thereby reducing the net lateral forces below the predetermined level and allowing the legs to deflect toward their pre-insertion configuration.

These and other objects, features, and advantages of the present invention will appear more fully from the following description of the exemplary embodiments, taken in conjunction with the accompanying drawings.

DETAILED DESCRIPTION OF THE INVENTION

Figure 1:
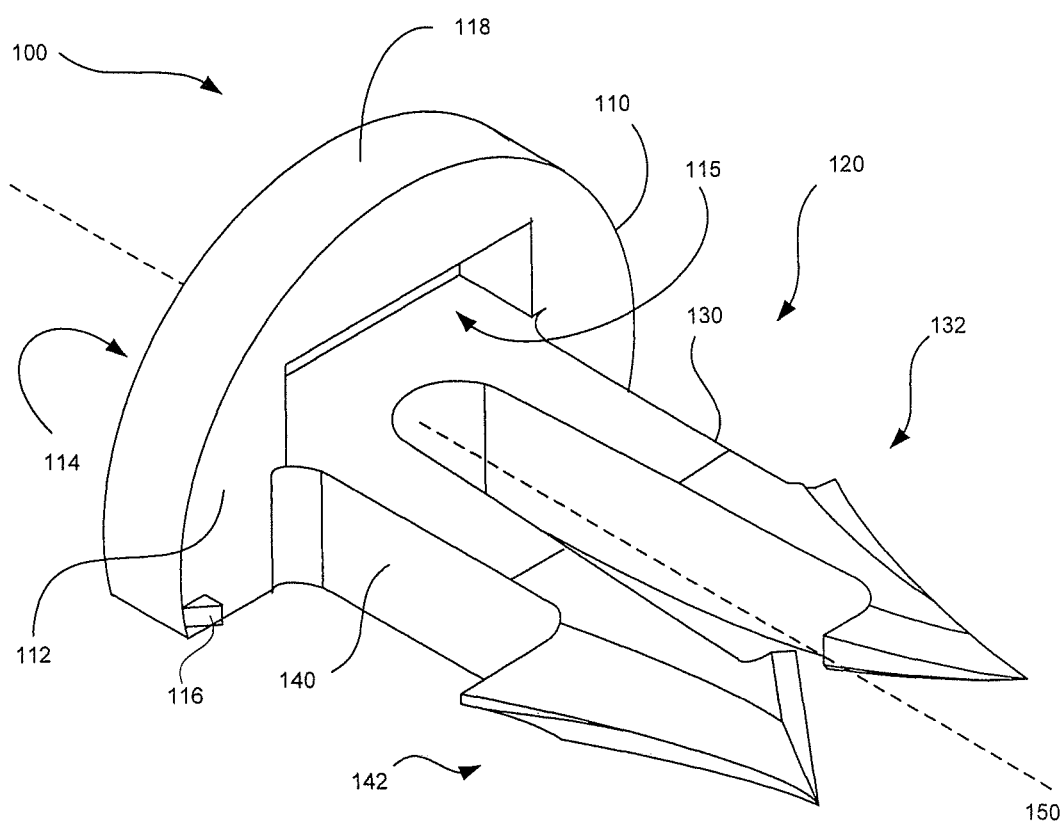
FIG. 1 is a perspective view of a fastener according to an exemplary embodiment of the invention.

Hereinafter, aspects of the invention in accordance with various exemplary embodiments will be described. As used herein, any term in the singular may be interpreted to be in the plural, and alternatively, any term in the plural may be interpreted to be in the singular.

As used herein, the term "proximal" refers to the portion of a fastener or fastener drive apparatus closest to the user (i.e., the person inserting the fastener), while the term "distal" refers to the portion of a fastener or fastener drive apparatus furthest from the user.

The fasteners of the invention are generally configured to secure body tissue to body tissue, or to secure another material, such as a mesh, to body tissue. For example, a fastener of the invention may be used as a tack to secure a mesh structure to body tissue in a hernia repair procedure. Accordingly, the embodiments included herein may be illustrated and described in reference to devices and methods used in conjunction with hernia repair. Thus, in describing the exemplary embodiments, the fasteners may be referred to as tacks or hernia mesh tacks and the drive apparatus used to deploy the fasteners may be referred to as a tack drive apparatus. It will be understood by those of ordinary skill in the art that the embodiments of the invention are not limited to hernia-related procedures and are applicable to various other surgical procedures that require the use of fasteners.

The present invention provides fasteners that exhibit retention performance superior to existing surgical tacks. This is accomplished by configuring the fastener to deform from an initial, static configuration in a predictable manner during insertion and then to return to the original configuration after insertion is complete. This allows the insertion cross-section, or footprint, of the fastener to be different from its post-insertion foot print, which, in turn, allows the use of highly secure anchoring elements that would otherwise be unusable or impractical due to the forces required and consequent trauma caused during insertion.

The exemplary fastener 100 shown in FIGS. 1-6 will be used to illustrate aspects of the invention. The fasteners of the invention are of the axial insertion or "push" type and are configured for serial deployment by an applicator. The fastener 100 has a head, or head portion, 110 and an anchoring portion 120 extending from the distal surface 112 of the head 110. The anchoring portion 120 is configured to penetrate tissue when a force having a distally directed component parallel to the longitudinal axis 150 is applied to the head 110 and then to securely anchor the fastener 100 to the tissue after penetration. The anchoring portion 120 includes first and second legs 130, 140 attached to the head 110 by a base portion 122. It will be understood that fasteners according to some embodiments of the invention may have three or more legs, but all will have at least first and second legs. The first leg 130 has a stem 131 and an anchoring element 132 comprising an inwardly extending barb 134 and an outwardly extending barb 136, and the second leg 140 has a stem 141 and an anchoring element 142 comprising an inwardly extending barb 144 and an outwardly extending barb 146. As will be discussed in more detail hereafter, other fastener embodiments of the invention may have different anchoring elements with more barbs, fewer barbs or even no barbs.

The anchoring portion 120 of the fastener 100 is geometrically structured so that when a distal insertion force $F_1$ is applied, it imparts a velocity V to the fastener 100 and causes the anchoring elements 132, 142 to penetrate tissue. The compression of the tissue surrounding the anchoring elements 132, 142 and the leg stems 131, 141 as they penetrate into the tissue 10 produces a net lateral force $F_C$ on each leg. The magnitude and distribution of this force will be a function of the geometry of the anchoring elements 132, 142, the degree to which the tissue is compressed prior to insertion (e.g., due to the pressing of the applicator against the surface of the tissue), the distal insertion force and the velocity/momentum of the fastener 100 during penetration.

Figure 3:
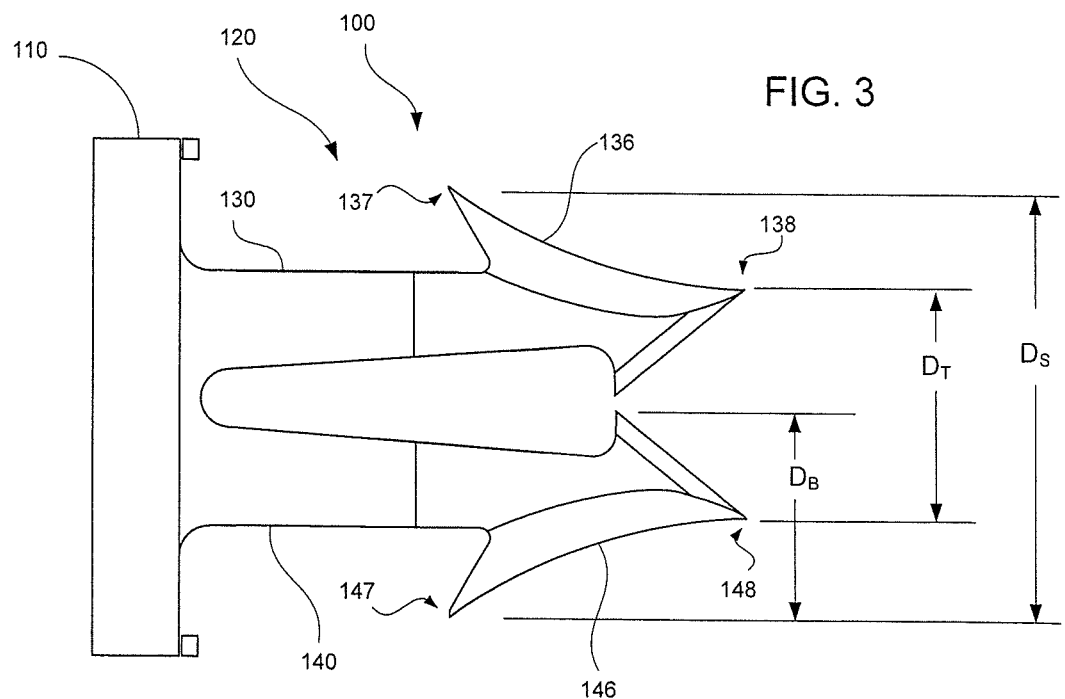
FIG. 3 is a top view of the fastener of FIG. 1.
Figure 4:
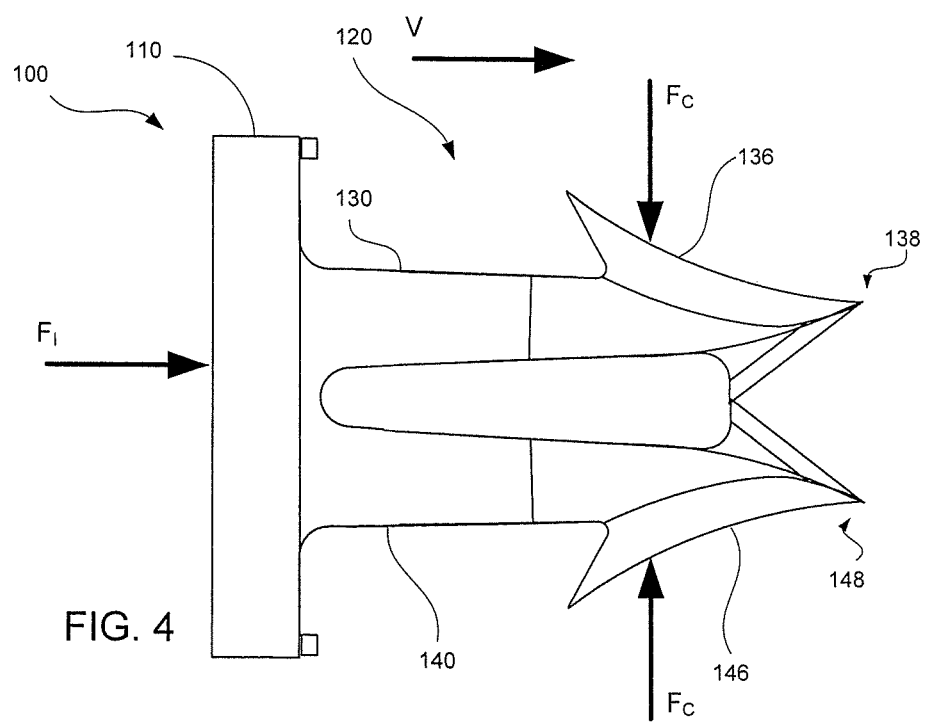
FIG. 4 top view of a fastener according to an embodiment of the invention in a deformed configuration produced by insertion forces.
Figure 5:
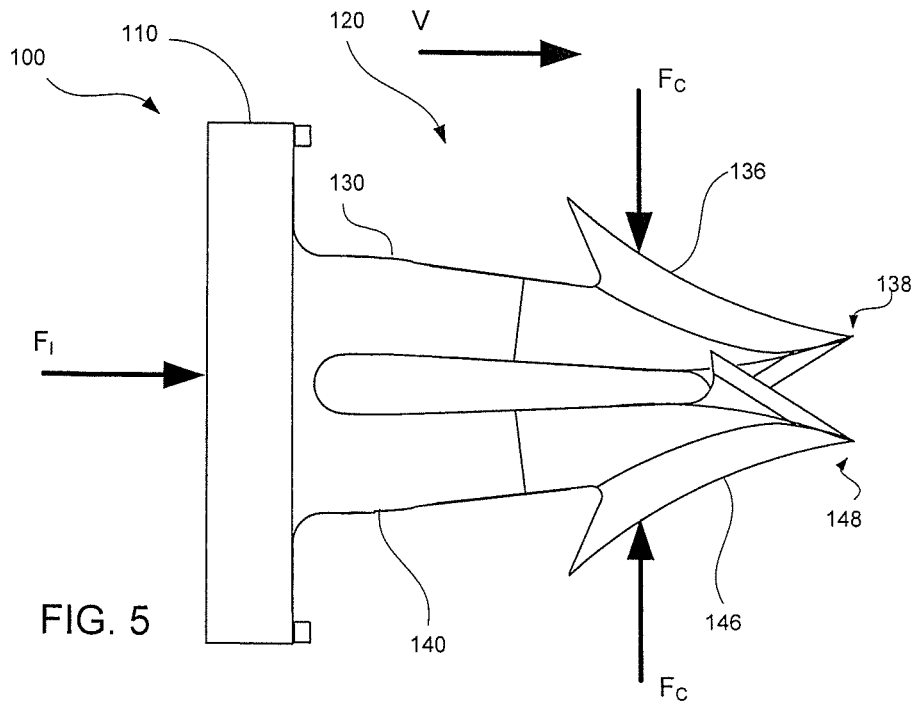
FIG. 5 top view of a fastener according to an embodiment of the invention in a deformed configuration produced by insertion forces.

The velocity of the fastener 100 may play a significant role in the net lateral force. When a high impulse load is applied to the fastener 100 so as to produce a high insertion speed, the effect is to increase the resistive force in the tissue, the lateral component of which adds to the net lateral force resulting from the impulsive insertion force itself. The net effect is a dynamic loading of the fastener 100 resulting from a complex interaction between the cutting of the tissue, the tissue's resistance to penetration/cutting, and the structural response of the anchoring portion 120 of the fastener 100. The inventors have found that the geometry and the material of the fastener 100 may be selected and configured to produce a predetermined net lateral force. The predetermined net lateral force may be established so as to exceed a threshold bending level $F_C$, thereby causing a predetermined bending deformation of the legs 130, 140 of the fastener 100, as shown in FIGS. 3-5. Among other things, this deformation may change the distance $D_T$ between distal tips 138, 148. In some embodiments, like that of the exemplary fastener 100, the deformation of the legs causes changes in other significant geometrical aspects of the anchoring elements. In the fastener 100, for example, the bending deformation of the legs causes a reduction in the overall span $D_S$ of the anchoring portion 120. Due to the angle change at the distal end 133, 143 of the stems 131, 141, the deformation also changes the angle of presentation of the leading edges of the anchoring elements and the effective span $D_B$ of each anchoring element.

It will be appreciated that the above-described deformation can be produced even if there is no continuing insertion force being applied to the fastener 100. The net lateral force may result only from the momentum of the fastener 100 and the compression of the tissue. As the fastener's momentum decreases, the lateral force is reduced.

Upon full insertion, the longitudinal forces resulting from the insertion force and fastener momentum are reduced to zero, which reduces the lateral compressive force $F_C$. Removal of pressure on the tissue to allow it to decompress may further reduce the lateral force $F_C$. When the lateral force $F_C$ is reduced, the resilient nature of the material used in the fastener legs 130, 140 biases them back toward the original pre-insertion configuration shown in FIGS. 1, 2 and 3. This bias causes a lateral motion of the anchoring elements in a direction opposite that of the deformation that occurred during insertion.

The anchoring elements 132 may be configured to take advantage of this post-insertion lateral motion. In the fastener 100, for example, the lateral forces $F_C$ act in an inward direction during insertion, thereby causing the legs 130, 140 to bend inward. This reduces the overall span $D_S$ of the penetrating/cutting portion of the fastener 100. Once the anchoring portion 120 has been inserted and the insertion and compression forces are removed, the biasing force of the resilient leg causes the insertion deformation to be reversed, thereby widening the span $D_S$ again. The result of the restorative motion is a lateral motion of the outwardly facing barbs 136, 146 into tissue that was not cut during insertion. This serves to securely anchor the anchoring elements of both legs 130, 140.

FIG. 4 illustrates a leg deformation in which the opposing inwardly extending barbs 134, 144 do not extend past one another. The legs 130, 140 may, however, be configured so that the anchoring elements 132, 142 may overlap as shown in FIG. 5. This allows a greater deflection of the distal ends of the legs 130, 140 and greater restorative lateral motion of the anchoring elements 132, 142 when the net lateral force is reduced or removed. In such an embodiment, the deformed configuration shown in FIG. 4 may be seen as an intermediate level of deformation.

It will be understood that the restoring force in the fastener legs is preferably sufficient to return the fastener 100 to its original geometry, thereby maximizing the lateral anchoring motion. This, however, is not a requirement to take advantage of the added anchoring capability of the invention. It will also be understood that while the anchoring portion is preferably configured so that the net lateral forces and, thus, the bending deformation on both legs are directed inward in opposing fashion, the fastening portion could instead be configured so that the lateral forces and bending deformation are directed outward in opposite directions, or in the same direction, which would be outward on one leg and inward on the other.

Figure 6:
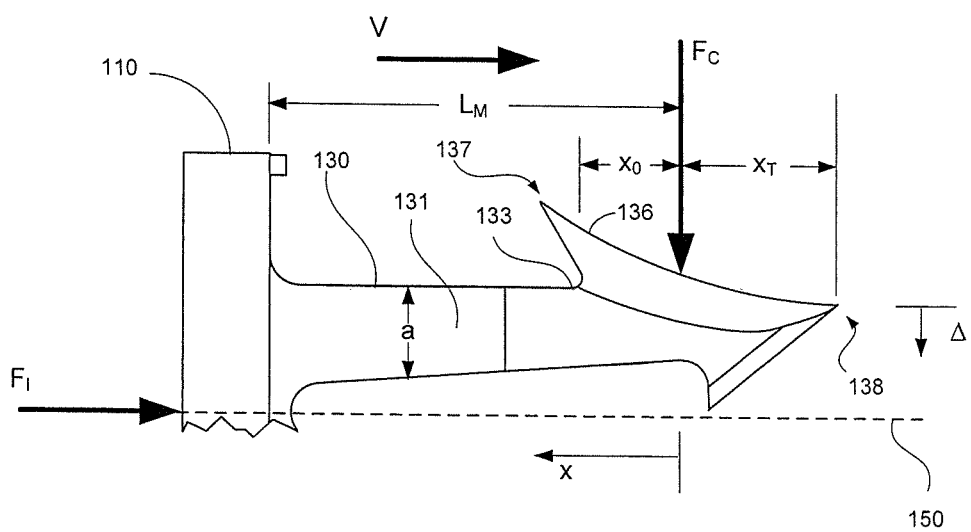
FIG. 6 is a partial top view of a fastener according to an embodiment of the invention.

The lateral deflection experienced at any point along the leg of a fastener is a function of the geometry and the material properties of the leg. This deflection may be calculated as a function of the magnitude of the net lateral force using a beam approximation. With reference to FIG. 6, the leg 130 of the fastener 100 may be treated as a beam attached to the head 110. The lateral force $F_C$ represents the net lateral force produced by the reactive compression force of the tissue against the blade surfaces of the anchoring element 132. The net lateral force produces an effective moment about the attachment point that produces bending and, thus, a lateral deflection $\Delta$ at every point along the leg stem 131. Every point along the anchoring element 132 is also deflected, but there is no significant bending.

The deflection at any point along the leg stem 131 between the head 110 and the distal stem end 133 (the proximal end of the anchoring element 132) may be approximated according to the following:

$$\Delta = (2F_C^2/Ea^4)(3L_M - x)$$ Eq 1:

where E is the elastic modulus, "a" is the width of the stem, $L_M$ is the effective moment arm of the net lateral force $F_C$, and x is the distance along the longitudinal axis 150 measured from the effective point of application of the net lateral force $F_C$. For simplicity, the cross-section of the stem 131 is assumed to be constant with a square profile. It will be understood that the maximum deflection of stem 131 occurs at the distal stem end 133 where $x = x_0$.

The maximum deflection anywhere on the anchoring element 132 occurs at its distal-most tip 138. This deflection may be approximated according to the following:

$$\Delta_{TIP} = (2F_C L_M^2/Ea^4)(2L_M + 3x_T)$$ Eq 2:

where $x_T$ is the distance along the longitudinal axis 150 from the effective point of application of the net lateral force $F_C$ to the distal tip 138 of the anchoring element 132.

For purposes of this example, the material used to form at least the anchoring portion 120 of a fastener 100 is assumed to be formed from a blend of polylactic acid (PLA) and polyglycolic acid (PGA) providing an elastic modulus E of $0.3 \times 10^6$ psi. For a fastener 100 with a typical stem dimension "a" of 0.022 in., a net lateral force $F_C$ of 0.1 lb. and an effective moment arm $L_M$ of 0.117 in., Eq. 1 provides an estimated deflection A at the distal stem end 133 of 0.009 in. If the distance between the effective application point of the lateral force and the distal tip 138 is 0.04 in., the lateral deflection of the distal tip 138 will be 0.013 in.

The above calculations would also apply to the other leg 140, with the deflections being in the opposite direction. Thus, it can be seen that a typical lateral compressive force acting on the anchoring elements 132, 142 may result in a reduction of the tip-to-tip span $D_T$ of 0.026 in. Of course, the overall span $D_S$ of the anchoring portion is also reduced. Because in this embodiment, the outer tips 137, 147 of the outer barbs 136, 146 are slightly further from the effective application point than are the distal stem ends 133, 143, their deflection will be similar to but slightly less than the deflection at the distal stem end. It can be seen, however, that a reduction of the overall span $D_S$ (and, thus the overall penetration footprint of the fastener 100) on the order of 0.018 in. is readily achievable. For a typical fastener 100, this would represent a 10-15% reduction in the length of the incision into the tissue. Moreover, it provides significant room for expansion of the anchoring elements 132, 142 into uncut tissue when the lateral compressive force is removed.

An approximation of the bending stress within the stem portions 131, 141 can also be calculated based on beam theory:

$$\sigma = (6F_C/a^4)(L_M - x)$$ Eq 3:

where $\sigma$ is the stress at a distance x from the application point of the net lateral force. For the example fastener 100 described above, a net lateral force $F_C$ of 0.1 lb. and an effective moment arm $L_M$ of 0.117 in., the maximum stress $\sigma_{max}$ would be 2600 psi. Given a yield strength of 6000 psi, the exemplary fastener would thus have a safety factor of 2.3.

Figure 7A:
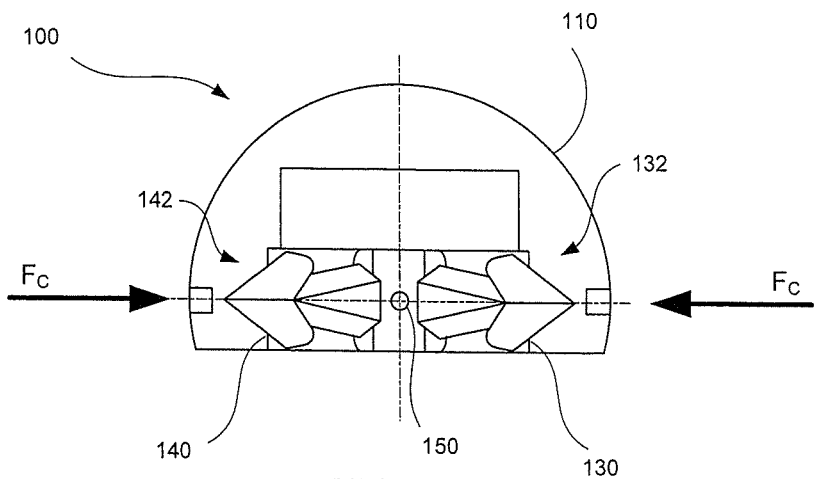
FIGS. 7A, 7B, and 7C are schematic end views of multiple leg fasteners according to embodiments of the invention.
Figure 7B:
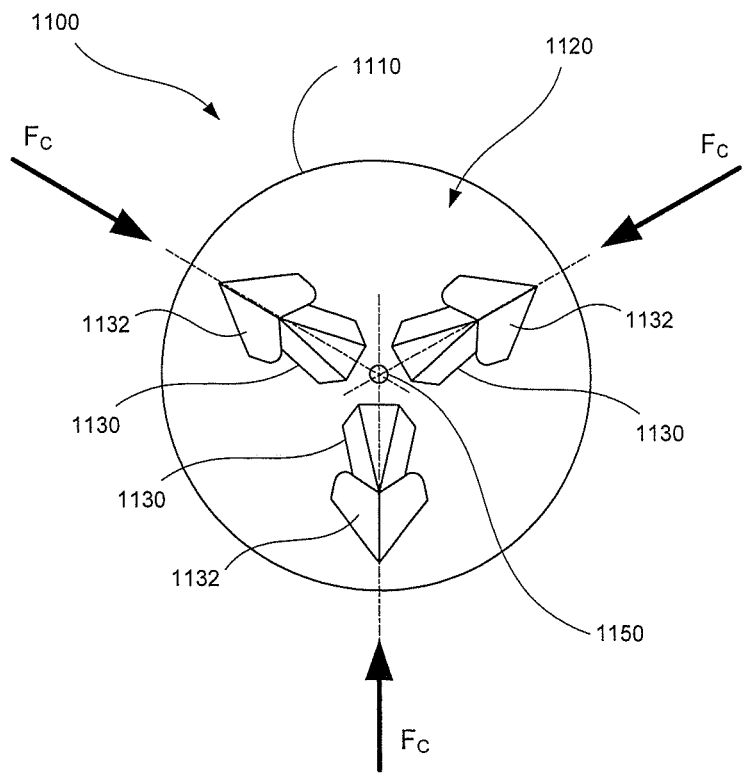
Figure 7C:
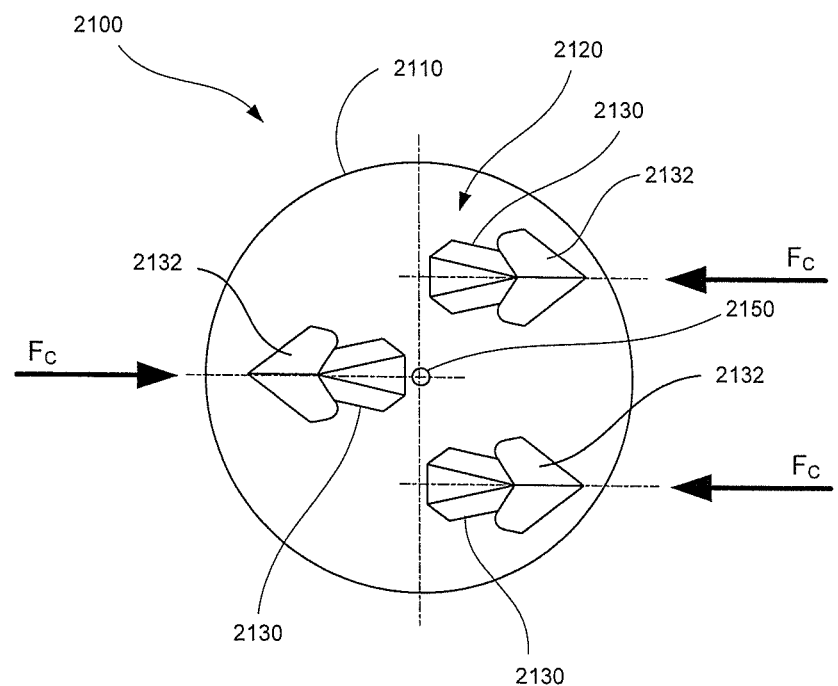

It will be understood that "lateral" as used herein is intended to mean a direction that is generally orthogonal to a plane through the longitudinal axis of the fastener. An inwardly directed lateral force would be directed toward this plane and an outwardly directed lateral force would be directed away from this plane. In the illustrative dual-leg fastener 100, the lateral forces $F_C$ on the two legs are inwardly directed in the same plane but in opposite directions (i.e., toward one another), as shown in FIG. 7A. In embodiments in which the legs are not arranged in a coplanar fashion, the lateral forces on the legs would not be coplanar. FIG. 7B shows a schematic representation of a fastener 1100 having a circular head 1110 and an anchoring portion 1120 comprising three similar distally extending legs 1130, each having a barbed anchoring element 1132. In this embodiment, the three legs are arranged equidistantly from the longitudinal axis 1150. FIG. 7C schematically illustrates another multi-leg configuration. In this embodiment, a fastener 2100 also has a circular head 2110 and an anchoring portion 2120 comprising three similar distally extending legs 2130, each having a barbed anchoring element 2132. Again, the anchoring elements 1132 may be similar to those of any fastener embodiment disclosed herein. In this embodiment, however, the three legs 2130 are arranged parallel to one another in a staggered configuration. The anchoring elements are configured so that the net lateral force $F_C$ on one of the legs 1132 is in one direction and net lateral force $F_C$ on each of the other two legs 1132 is in the opposite direction. A variation on this approach would be to provide a fourth leg so that two anchoring elements could be configured to provide net lateral forces in each direction. Any practical number and configuration of legs and anchoring elements may be used.

It will be understood that the specific features of the anchoring portion of the fasteners of the invention can be tailored to provide (1) a desired net lateral force, (2) a desired deformation/deflection in response to the net lateral force, and (3) a desired lateral penetration upon reduction of the net lateral force. It will also be understood, however, that the fastener must have sufficient rigidity and strength to allow penetration and anchoring of materials such as a hernia repair mesh.

The initial insertion force required to produce the net lateral forces needed to deform such a fastener is considerably higher than the forces typically provided by known applicator mechanisms. Moreover, the slow, steady insertion force provided by conventional insertion mechanisms will not produce the dynamic loading necessary to deform the fasteners of the invention. The inventors have found, however, that the required dynamic loading may be provided by subjecting the semi-rigid fasteners of the invention to a short duration impact load such as may be delivered by the applicator described in U.S. application Ser. No. 12/844,260 ("'260 Application"), the disclosure of which is incorporated herein by reference in its entirety. This technique, sometimes referred to as impulse loading, produces a very high release force that causes high speed ejection and penetration of the anchoring portion of the fastener through repair materials (such as a hernia repair mesh) and into the tissue below, even when the tissue is compressed.

The high fastener energy obtained from a high impulse driver such as that of the '260 Application also has the benefit of providing good penetration performance in spite of small errors such as low application pressure or off-angle pressures by the applicator user. Surgeons of various skill levels can achieve equally acceptable fastener installation performance with an impulse driver and the dual leg fasteners of the invention.

It will be understood that the fasteners of the invention may be specifically designed to take advantage of high impulse forces. Of particular interest, are impulses in a range of 24 to 100 lb-sec. Such impulse levels are delivered over time intervals on the order of 0.1 to 1.0 msecs.

Figure 2:
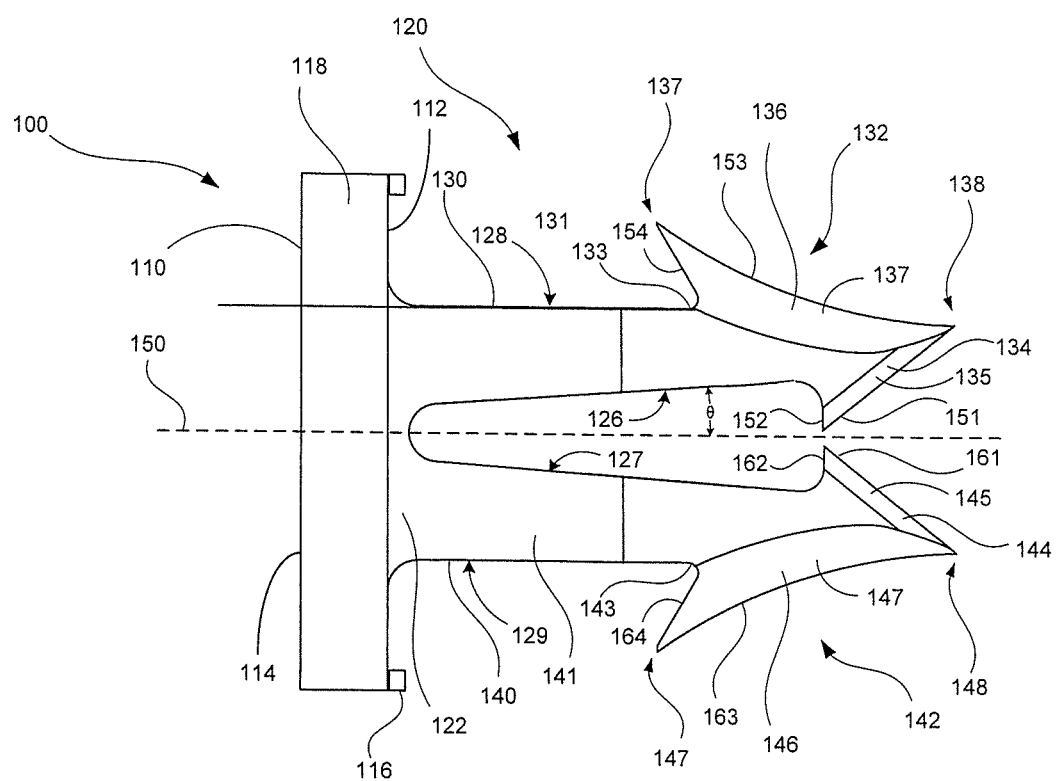
FIG. 2 is a top view of the fastener of FIG. 1.

A wide variety of geometric parameters are available to the designer to tailor the fasteners of the invention to produce the desired combination of penetration, lateral insertion force, deformation and restoration. With reference in particular to FIGS. 1 and 2, the illustrative fastener 100 is a dual leg fastener, each leg 130, 140 of which has an anchoring element 132, 142 has a pair of barbs 134, 136 and 144, 146. The inward barbs 134, 144 are each formed by an upper facet 135, 145 and a lower facet (not shown) which meet along a sharp, straight or nearly straight leading edge 151, 161 and a relatively blunt trailing (proximal) edge 152, 162. The outward barbs 136, 146 are each formed by an upper facet 137, 147 and a lower facet (not shown) which meet along a sharp, concave leading (distal) edge 153, 163 and a relatively blunt trailing (proximal) edge 154, 164. In the illustrated embodiment, the leading edges 151, 153 of the barbs 134, 136 of the first leg 130 meet at a single point to form the distal tip 138 of the anchoring element 132 and the leading edges 161, 163 of the barbs 144, 146 of the second leg 140 meet at a single point to form the distal tip 148. In other embodiments, the barbs and leading edges for each leg may be slightly offset from one another as in the single leg fasteners disclosed in the '260 Application. The leading edges 153, 163 and the trailing edges 154, 164 of the outer barbs 136, 146 meet to form the outer tips 137, 147.

As can be readily seen, the outward extending barbs 136, 146 of the fastener 100 are significantly larger than the inward extending barbs 134, 144 in order to produce an inwardly directed net lateral force during penetration. The relative size of the inward and outward barbs and the geometry of their leading edges can be tailored to particular dynamic loading scenarios to produce a particular net lateral force and insertion incision footprint. The amount of deformation may be tailored through the geometry of the leg stems 131, 141. For example, while it is possible to configure the fasteners of the invention with both lateral surfaces of each leg stem 131, 141 to be essentially parallel to the longitudinal access, it has been found that establishing a desired deformation response to a net lateral force on the distal end of the leg can be facilitated by angling one or both lateral leg stem surfaces slightly. In particular, the bending behavior may be facilitated by angling at least one of the lateral surfaces in the direction of the desired deflection of the distal tip of the leg. As shown in the illustrated embodiment, the stems 131, 141 of the exemplary fastener 100 have inward facing surfaces 126, 127 that provide a lateral angle θ with respect to the longitudinal axis 150. This angle may be in a range of 0-10 degrees and will typically be in a range of 3-5 degrees. In this embodiment, the outward facing lateral surfaces 128, 129 are substantially parallel to the longitudinal axis 150.

The cross-section of the leg stems 131, 141 may also be tailored to produce a desired bending response. In the illustrated embodiment, the cross-section at each point along the length of the stems 131, 141 is a square, the area of which decreases with distance from the base 122. In some embodiments, the cross-section may be held constant along some or all of the length of the leg stems 131, 141. It will be understood that other cross-sectional shapes may be used depending on the desired response and the desired rigidity of the fastener under non-dynamic loading conditions.

The head 110 of the fastener 100 is generally configured to provide a distal bearing surface 112 for engaging a tissue surface, a repair material such as a hernia repair mesh, or both. In particular applications, the head may be configured to sandwich a repair material between the distal surface 112 and the tissue in which the anchoring portion 120 of the fastener 100 is embedded. The specific geometry of the fastener head 110 may be determined in combination with the design of the applicator that will be used to deploy the fastener 100. For example, in the illustrated embodiment, the head 110 has an arcuate surface 118 connecting the distal surface 112 to a flat proximal surface 114. This arcuate surface 118 is complementary to the inner surface of a deployment tube in an actuator like that described in the '260 Application. Other features of the head 110 may also be tailored to a particular actuation mechanism. For example the head 110 may have a passage 115 formed therethrough to allow the fastener to slide along a beam such as the indexer of the applicator in the '260 Application. As another example, the proximal surface 114 may be configured for contact by one or more elements of the applicator to impart an impelling force to the fastener 100 for ejection from the applicator and insertion into tissue. The head 110 may also optionally include retention elements such as the tabs 116, which are configured to assist in anchoring repair materials to a tissue surface.

Figure 8:
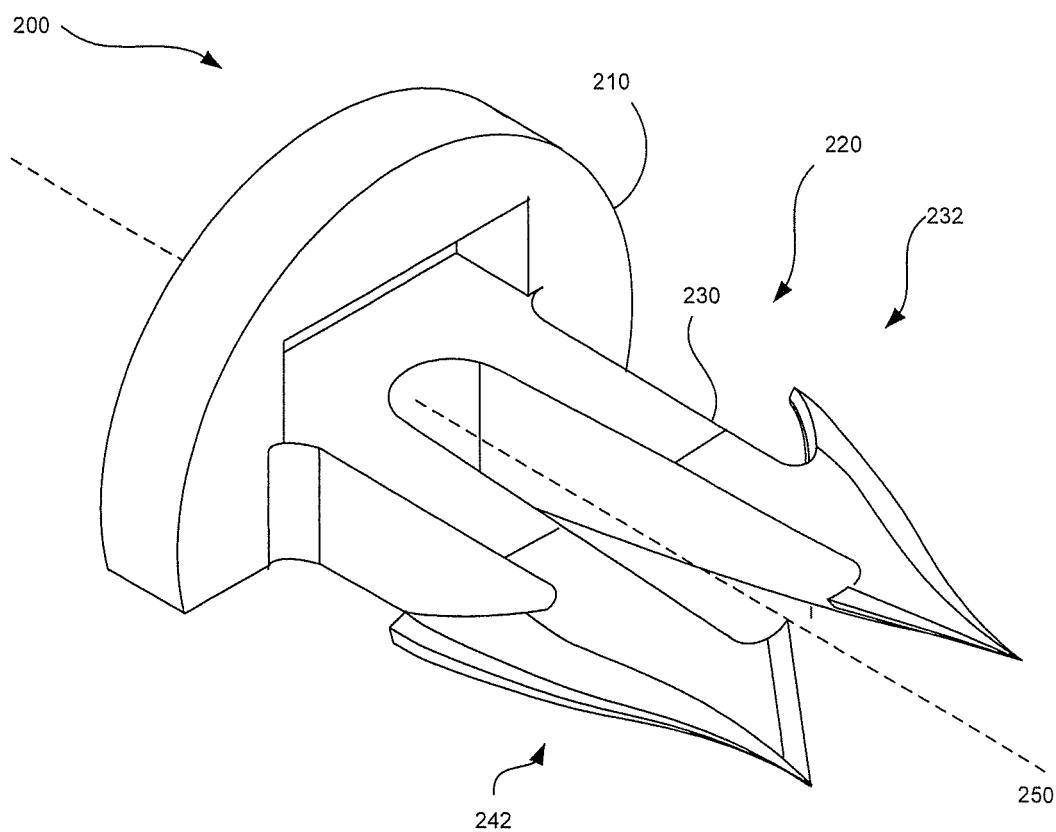
FIG. 8 is a perspective view of a fastener according to an exemplary embodiment of the invention.
Figure 9:
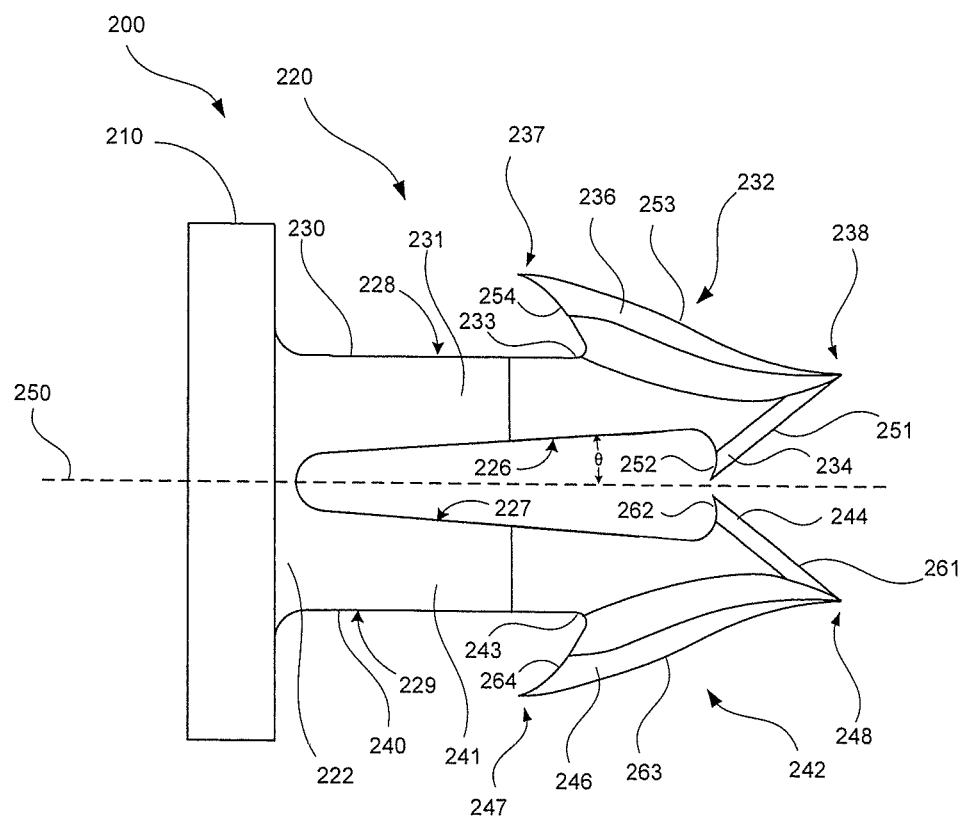
FIG. 9 is a top view of the fastener of FIG. 8.

Another illustrative multi-leg fastener 200 having multiple barbs on each leg is illustrated in FIGS. 8 and 9. Like the previous embodiment, the fastener 200 has a head, or head portion, 210 and an anchoring portion 220 extending from the distal bearing surface 212 of the head 210. The anchoring portion 220 is configured to penetrate tissue when a force having a distally directed component parallel to the longitudinal axis 250 is applied to the head 210 and then to securely anchor the fastener 200 to the tissue after penetration. The anchoring portion 220 includes first and second legs 230, 240 attached to the head 210 by a base portion 222. The first leg 230 has a stem 231 and an anchoring element 232 comprising an inwardly extending barb 234 and an outwardly extending barb 236, and the second leg 240 has a stem 241 and an anchoring element 242 comprising an inwardly extending barb 244 and an outwardly extending barb 246.

The inward barbs 234, 244 each have straight or nearly straight leading edge 251, 261 and a relatively blunt trailing (proximal) edge 252, 262. The outward barbs 236, 246 each have a leading (distal) edge 253, 263 and a relatively blunt trailing (proximal) edge 254, 264. In the illustrated embodiment, the leading edges 251, 253 of the barbs 234, 236 of the first leg 230 meet at a single point to form the distal tip 238 of the anchoring element 232, and the leading edges 261, 263 of the barbs 244, 246 of the second leg 240 meet at a single point to form the distal tip 248. In other embodiments, the barbs and leading edges for each leg may be slightly offset from one another as in the single leg fasteners disclosed in the '260 Application. The leading edges 253, 263 and the trailing edges 254, 264 of the outer barbs 236, 246 meet to form the distal (outer) tips 237, 247.

The outward barbs 236, 246 of the fastener 200 are formed so that their leading edges 253, 263 are in the shape of a reflexive curve that is concave near the distal barb tips 238, 248 and convex near the proximal tips 237, 247. The reflexive curve shape adds strength to the proximal portions of the barbs 236, 246 to better withstand the loads that may be experienced when the anchoring elements 232, 242 are forced through mesh or other material. This shape is also believed to increase the surface area over which the inward lateral compressive force of the tissue acts and thus to increase the net lateral force. It is also thought to enhance the lateral cutting that occurs when the deformed fastener 200 is biased back toward its unstressed/undeformed shape upon reduction or removal of the net lateral force. The exact shape of the curve may be tailored to particular tissue types and/or impulsive force levels.

As in the previous embodiment, the specific configuration of the leg stems 231, 241 may be tailored to provide a desired bending response. For example, the stems 231, 241 of the exemplary fastener 200 may have inward facing surfaces 226, 227 that provide a lateral angle θ with respect to the longitudinal axis 250. This angle may be in a range of 0-10 degrees and will typically be in a range of 3-5 degrees. In the illustrated embodiment, the outward facing lateral surfaces 228, 229 are substantially parallel to the longitudinal axis 250. The cross-section of the leg stems 231, 241 may also be tailored to produce a desired bending response.

In the illustrated embodiment, the cross-section at each point along the length of the stems 231, 241 is a square, the area of which decreases with distance from the base 222. In some embodiments, the cross-section may be held constant along some or all of the length of the leg stems 231, 241. It will be understood that other cross-sectional shapes may be used depending on the desired response and the desired rigidity of the fastener under non-dynamic loading conditions.

Figure 10:
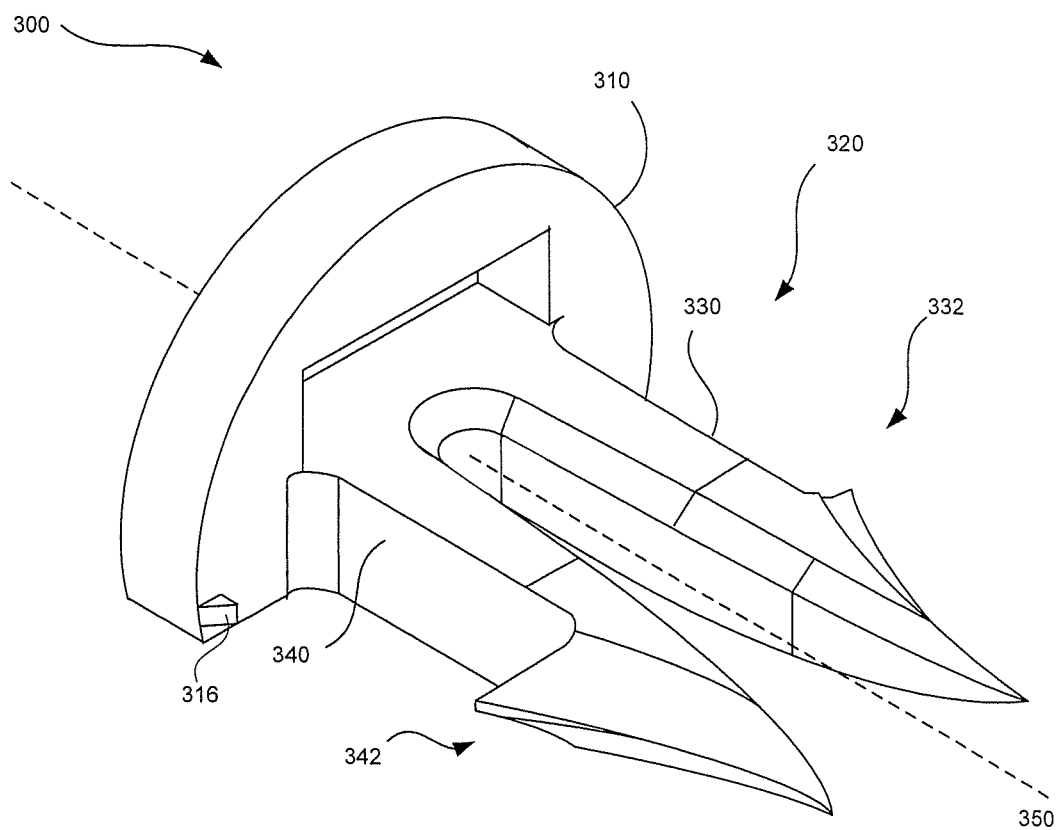
FIG. 10 is a perspective view of a fastener according to an exemplary embodiment of the invention.
Figure 11:
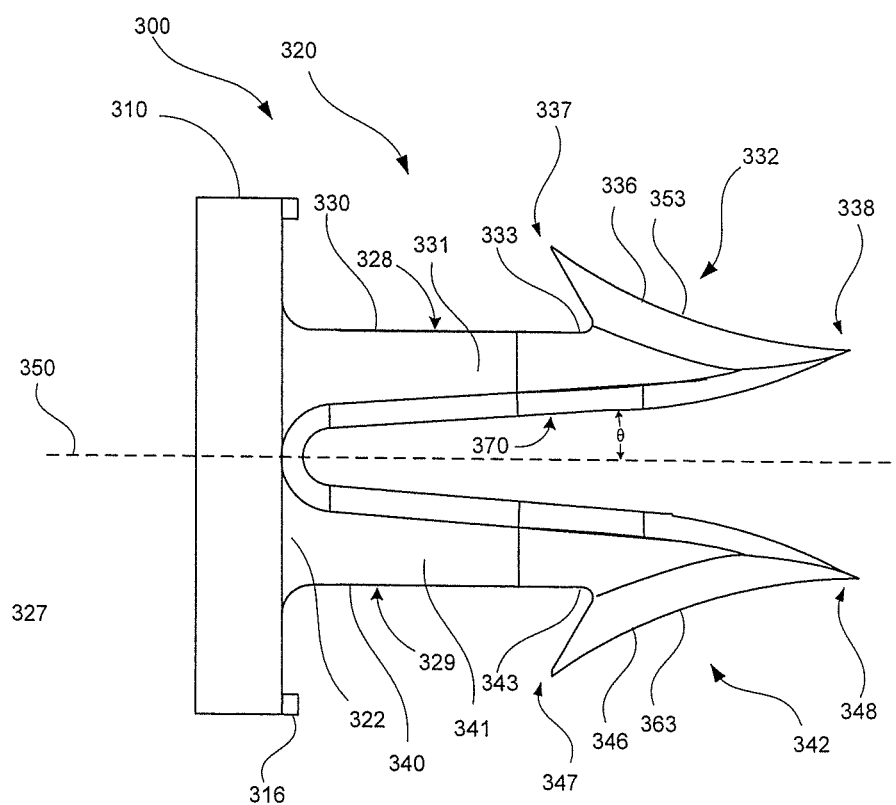
FIG. 11 is a top view of the fastener of FIG. 10.

Another illustrative multi-leg fastener 300 is illustrated in FIGS. 10 and 11. Unlike the previous embodiments, the anchoring elements of the fastener 300 each have only a single, outward extending barb. The fastener 300 has a head, or head portion, 310 and an anchoring portion 320 extending from the distal bearing surface 312 of the head 310. The anchoring portion 320 is configured to penetrate tissue when a force having a distally directed component parallel to the longitudinal axis 350 is applied to the head 310 and then to securely anchor the fastener 300 to the tissue after penetration. The anchoring portion 320 includes first and second legs 330, 340 attached to the head 310 by a base portion 322. The first leg 330 has a stem 331 and an anchoring element 332 comprising an outwardly extending barb 336, and the second leg 340 has a stem 341 and an anchoring element 342 comprising an outwardly extending barb 346. Each leg has an inner surface 370 that may be formed as a single flat or continuously curved facet (not shown) or as a plurality of flat or curved facets. The inner surface 370 tapers as it approaches the distal tips 338, 348 of the anchoring elements 332, 342.

The barbs 336, 346 each have a concave leading (distal) edge 353, 363 and a relatively blunt trailing (proximal) edge 354, 364. The leading edge 353 meets one of the tapered ends of the inner surface 370 at a single point to form the distal tip 338 of the anchoring element 332, and the leading edge 363 meets the other tapered end of the inner surface 370 at a single point to form the distal tip 348. The leading edges 353, 363 and the trailing edges 354, 364 of the barbs 336, 346 meet to form the distal (outer) tips 337, 347.

Although the leading edges 353, 363 of the barbs 336, 346 are illustrated with a concave configuration, it will be understood that the barbs 336, 346 (and also the outer barbs 136, 146 of the embodiment shown in FIGS. 1 and 2) may be formed so that the leading edges 353, 363 are in the shape of a reflexive curve similar to that shown for the fastener 200 of FIGS. 7 and 8. The exact shape of the curve may be tailored to particular tissue types and/or impulsive force levels.

As in the previous embodiments, the specific configuration of the leg stems 331, 341 may be tailored to provide a desired bending response. For example, the inner surface 370 provide a lateral angle θ with respect to the longitudinal axis 350. This angle may be in a range of 0-10 degrees and will typically be in a range of 3-5 degrees. In the illustrated embodiment, the outward facing lateral surfaces 328, 329 are substantially parallel to the longitudinal axis 350. The cross-section of the leg stems 331, 341 may also be tailored to produce a desired bending response. In the illustrated embodiment, the cross-section at each point along the length of the stems 331, 341 is a square, the area of which decreases with distance from the base 322. In some embodiments, the cross-section may be held constant along some or all of the length of the leg stems 331, 341. It will be understood that other cross-sectional shapes may be used depending on the desired response and the desired rigidity of the fastener under non-dynamic loading conditions.

Figure 12:
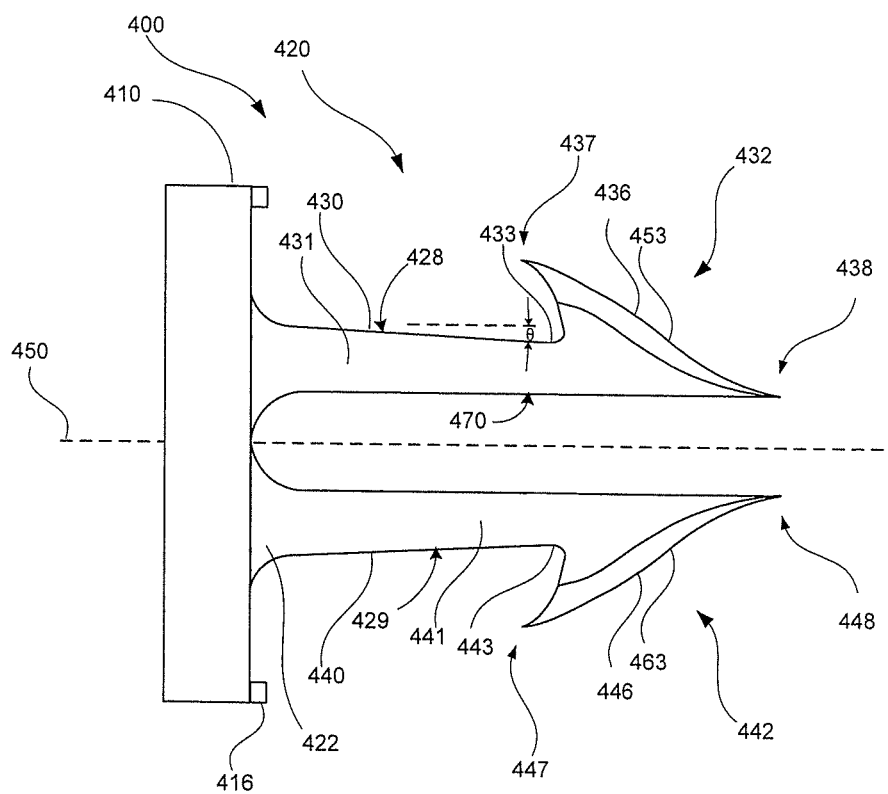
FIG. 12 is a top view of a fastener according to an exemplary embodiment of the invention.

Yet another illustrative multi-leg fastener 400 is illustrated in FIG. 12. Like the preceding embodiment, the anchoring elements of the fastener 400 each have only a single, outward extending barb. The fastener 400 has a head, or head portion, 410 and an anchoring portion 420 extending from the distal bearing surface 412 of the head 410. The anchoring portion 420 is configured to penetrate tissue when a force having a distally directed component parallel to the longitudinal axis 450 is applied to the head 410 and then to securely anchor the fastener 400 to the tissue after penetration. The anchoring portion 420 includes first and second legs 430, 440 attached to the head 410 by a base portion 422. The first leg 430 has a stem 431 and an anchoring element 432 comprising an outwardly extending barb 436, and the second leg 440 has a stem 441 and an anchoring element 442 comprising an outwardly extending barb 446. Each leg has an inner surface 470 that may be formed as a single flat or continuously curved facet (not shown) or as a plurality of flat or curved facets. The inner surface 470 tapers as it approaches the distal tips 438, 448 of the anchoring elements 432, 442.

The barbs 436, 446 each have a leading (distal) edge 453, 463 in the shape of a reflexive curve similar to that shown for the fastener 200 of FIGS. 7 and 8 and a relatively blunt trailing (proximal) edge 454, 464. The leading edge 453 meets one of the ends of the inner surface 470 at a single point to form the distal tip 438 of the anchoring element 432, and the leading edge 463 meets the other tapered end of the inner surface 470 at a single point to form the distal tip 448. The leading edges 453, 463 and the trailing edges 454, 464 of the barbs 436, 446 meet to form the distal (outer) tips 437, 447.

In the fastener 400, the straight sides of the inner surface 470 are parallel to the longitudinal axis 450. The outward facing lateral surfaces 428, 429, however, are angled inward at a lateral angle θ with respect to the longitudinal axis 450. This angle may be in a range of 0-10 degrees and will typically be in a range of 4-5 degrees. The cross-section of the leg stems 431, 441 may also be tailored to produce a desired bending response. In the illustrated embodiment, the cross-section at each point along the length of the stems 431, 441 is a square, the area of which decreases with distance from the base 422. In some embodiments, the cross-section may be held constant along some or all of the length of the leg stems 431, 441. It will be understood that other cross-sectional shapes may be used depending on the desired response and the desired rigidity of the fastener under non-dynamic loading conditions.

The exemplary embodiments illustrated in FIGS. 1-12 are each configured to provide an inwardly directed net lateral force on each fastener leg. As has been previously indicated, however, any of the above embodiments may be modified to produce an outwardly directed net lateral force, typically by swapping the positions of the inward and outward barbs or, in the case of the single barb per leg embodiment, switching the barb from an outer surface position to an inner surface position.

The elements of any of the fasteners of the invention may be made of any of various materials suitable for insertion into the human body. In various embodiments, portions of the fasteners may be made of biocompatible material, such as stainless steel, titanium or plastic. In some embodiments, the fasteners may include components made from or may be made entirely from molded thermoplastic materials. In certain exemplary embodiments, the fasteners may include or may be made entirely of bioabsorbable materials. Exemplary bioabsorbable materials include homopolymers and copolymers of lactide, glycolide, polyglycolide, polylactide, or various combinations or mixtures thereof. It will be understood that there are various suitable polymers and that each exhibits different absorption rates, and different shear and tensile strengths when molded.

In particular embodiments, the fasteners of the invention may be made of a blend of PLA and PGA in a ratio in a range of 65/35 PLA/PGA to 95/5 PLA/PGA. In a particularly suitable embodiment the ratio is 85/15 PLA/PGA. Other % combinations, or other materials are also possible.

In some embodiments, the head and the entire anchoring portion of the fastener may be formed from the same material. In other embodiments, some or all of the anchoring portion may be formed from a one or more different materials. For example, the barbs of the anchoring portion may be made of a different material than the stems of the legs and/or the tack head. In particular, the barbs may be made of a material having a different degree of rigidity than the material of the leg stems. More particularly, the material of the barbs may have a lower rigidity than the material of the leg stems.

It will be understood that the various components of the fasteners of the invention may be integrally formed as a single monolithic body or may be separately formed and adhered or otherwise attached to one another.

It will also be understood that the fasteners of the invention may be of any size suitable for insertion into the human body and suitable to provide a stable anchoring structure. For example, in various embodiments, the fasteners may have an effective overall length (measured longitudinally from the proximal head surface to the distal tips of the anchoring portion) in the range of about 4 mm to about 6 mm. In typical embodiments, the widest span of the anchoring elements in their undeformed configuration will be in the range of about 3 mm to about 5 mm.

FIGS. 13-17 illustrate the sequence of events in a method of applying a typical fastener according to an aspect of the invention. Although the illustrated example makes use of the fastener 100 of FIGS. 1 and 2, the described method applies equally to the other fastener embodiments. In FIG. 11, an applicator 900 having one or more fasteners 100 disposed therein is positioned adjacent tissue 10 at a desired location. In a typical configuration, the applicator 900 will have a tube 910 configured for receiving the fastener(s) 100 and having a distal end 920 from which the fastener(s) may be ejected. The applicator may have a mechanism (not shown) for imparting an insertion force $F_1$ that is maintained through some or all of the insertion process. Alternatively, the applicator may be configured to simply eject the fastener 100 with sufficient velocity to produce net lateral forces that deform the fastener during penetration.

The applicator may place the fastener 100 in a pre-insertion position adjacent the body tissue 10. As used in this context, the term adjacent is intended to include a case where the fastener 100 is placed in contact with or near the body tissue 10. It will be understood that a mesh or other repair material may be interposed between the body tissue 10 and the fastener 100 prior to insertion.

Figure 14:
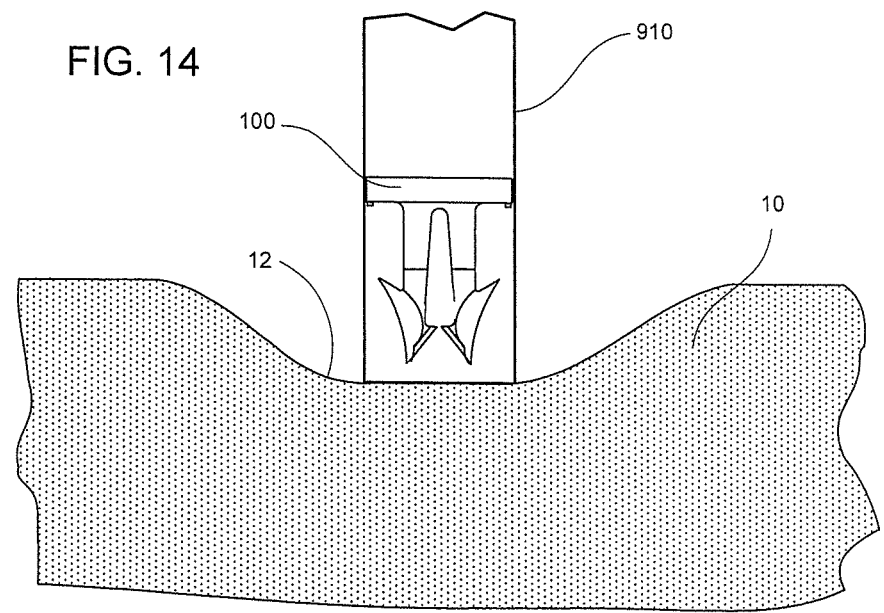
FIG. 14 is a schematic representation of a step in fastener insertion process according to an aspect of the invention.
Figure 15:
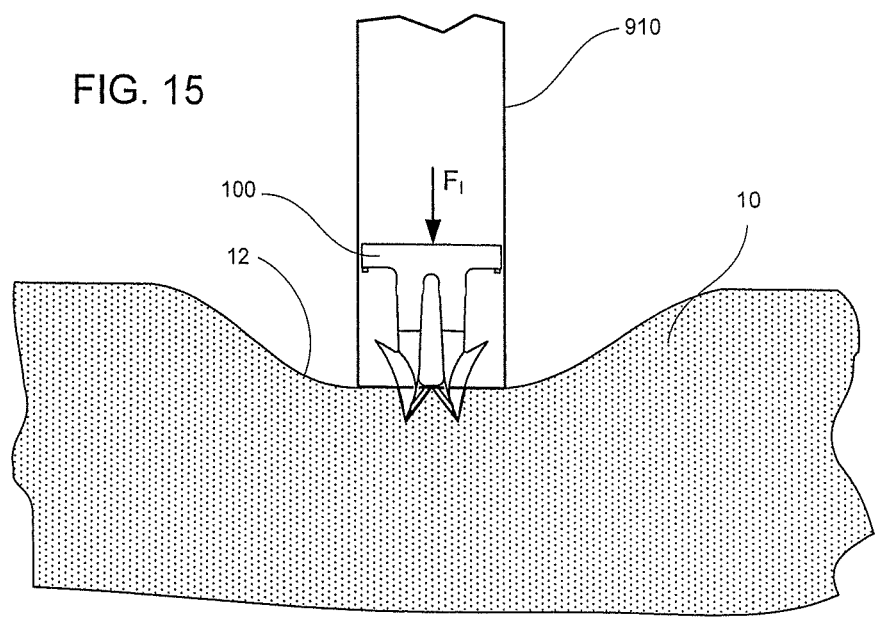
FIG. 15 is a schematic representation of a step in fastener insertion process according to an aspect of the invention.
Figure 16:
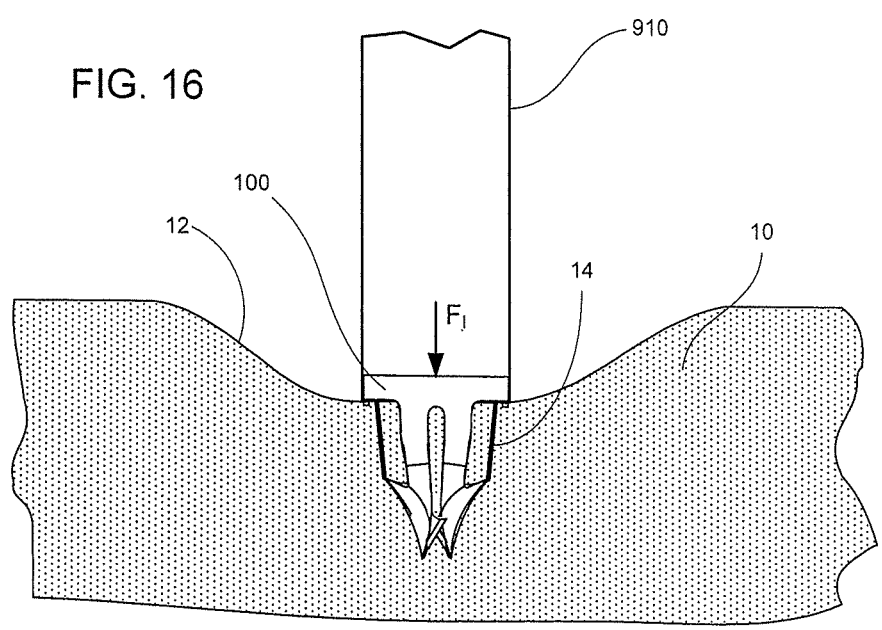
FIG. 16 is a schematic representation of a step in fastener insertion process according to an aspect of the invention.

As shown in FIG. 14, the user of the applicator 900 may press the applicator tube 910 down on the tissue 10, causing it to compress. The user may then activate the firing mechanism of the applicator 900 to impart an insertion force (e.g., an impulse load) and eject the fastener 100 as described above. FIG. 15 illustrates that as the fastener 100 is ejected, its anchoring portion begins to penetrate the compressed tissue. The resulting resistance by the tissue 10 causes the fastener to begin to deform. The amount of deformation at this stage may be similar to that shown in FIG. 4. FIG. 16 illustrates a point of maximum deformation similar to that shown in FIG. 5. It can be seen that as the anchoring portion of the fastener 100 penetrates the tissue 10, it's outward extending barbs 136 produce an incision 14, the width of which is determined in part by the amount of deflection of the blade tips and the resulting tip-to-tip span. It will be understood that the width of the incision 14 will also be affected by the degree to which the tissue stretches.

Figure 13:
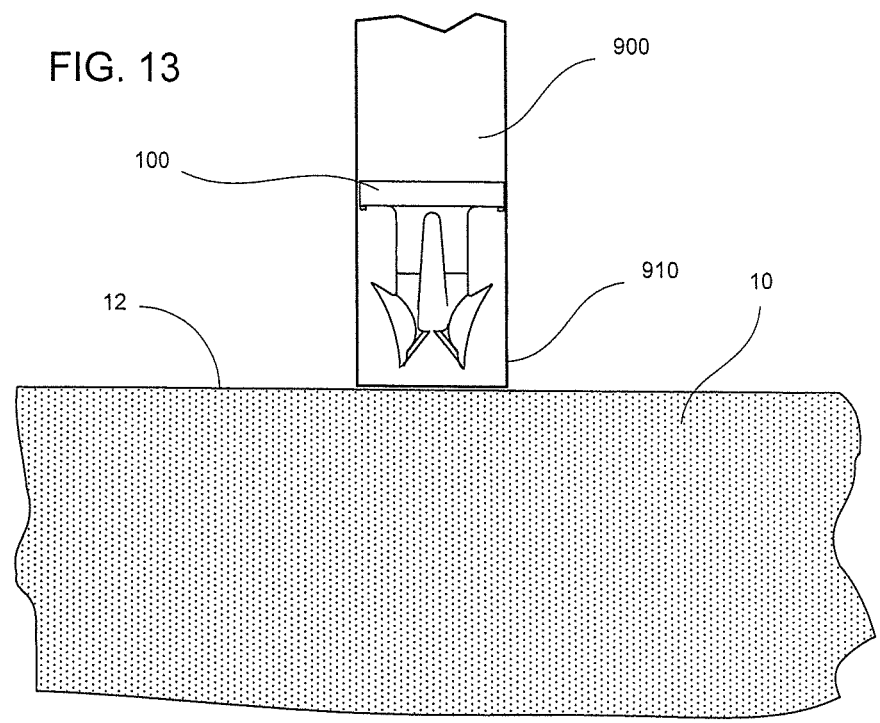
FIG. 13 is a schematic representation of a step in fastener insertion process according to an aspect of the invention.
Figure 17A:
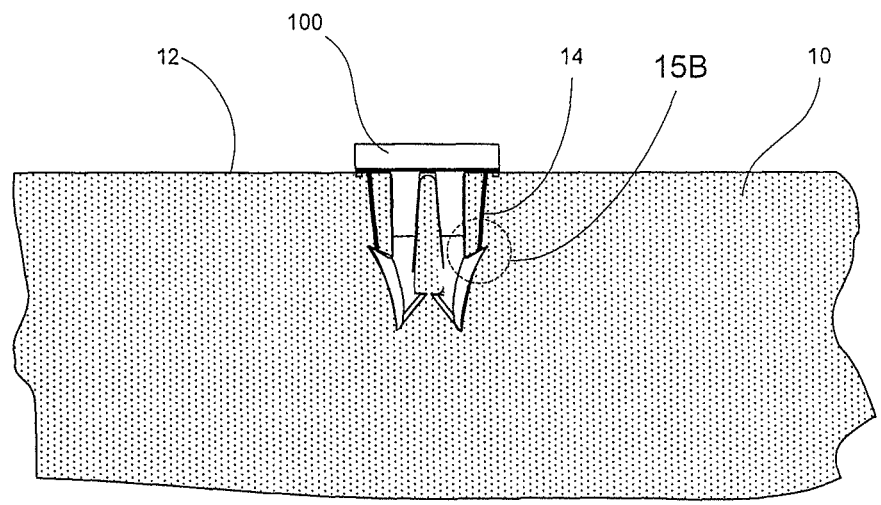
FIGS. 17A and 17B are section views illustrating a fastener according to an embodiment of the invention after insertion into tissue.
Figure 17B:
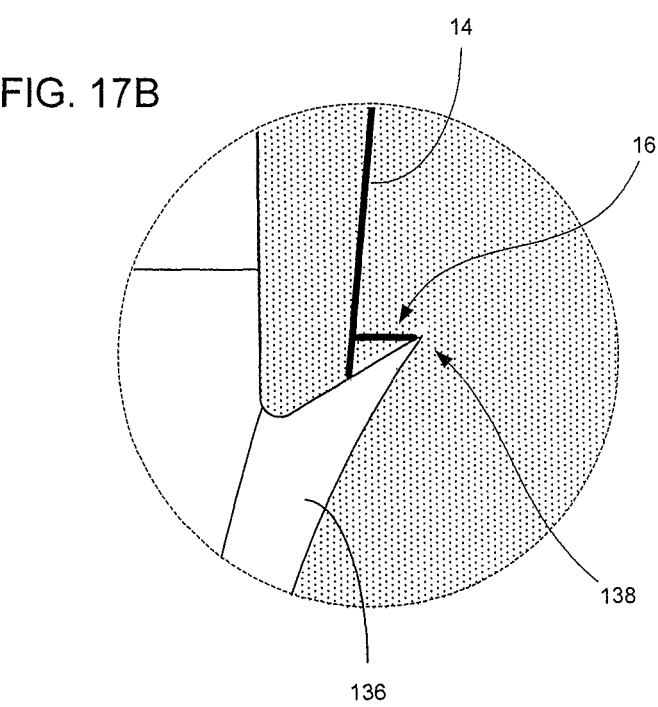

The fastener's penetration is stopped when the head of the fastener is seated against the surface 12 of the tissue 10. The applicator user then removes the applicator, which releases the compressive pressure on the tissue 10 as shown in FIGS. 17A and 17B. With any insertion force and penetration velocity stopped and the compressive lateral force removed, the fastener 100 returns to a configuration the same or similar to its original configuration as shown in FIGS. 3 and 13. The bias of the fastener legs back to their original state causes the outward barb tips 138 to move laterally into previously uncut tissue 16 as best seen in FIG. 17B. The effect is to embed the barbs 136 beneath undisturbed tissue and to prevent withdrawal of the barbs 136 along the path of the insertion incision 14.

The above-described lateral embedding significantly increases the force required to pull the fastener 100 out of the tissue 10 (i.e., the withdrawal force). It will be understood that the withdrawal force can be further increased through the design of the proximal edge of the barbs 136. One simple approach is to provide a relatively blunt edge to minimize its ability to slice through tissue when a withdrawal force is applied. Another approach is to maximize the surface area of the proximal edge normal to the withdrawal force. This, approach, however, will tend to reduce the sharpness of the angle forming the barb tip. The inventors have found, however, that the fastener legs may be designed to deform in a predetermined manner when subjected to high withdrawal loads. In particular, the legs may be designed so that when a high withdrawal force is applied, the anchoring elements tend to pivot in such a way that the proximal edge of the outward (or inward, if desired) facing barbs present a larger surface normal to the withdrawal force.

Figure 18A:
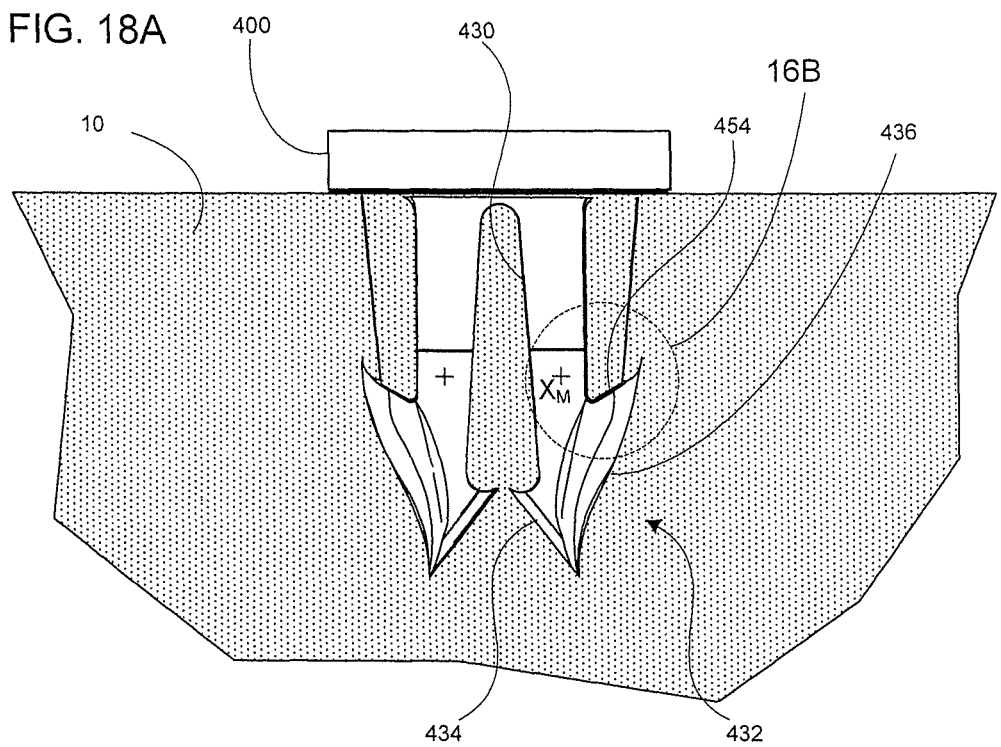
FIGS. 18A and 18B are section views illustrating a fastener according to an embodiment of the invention after insertion into tissue.
Figure 18B:
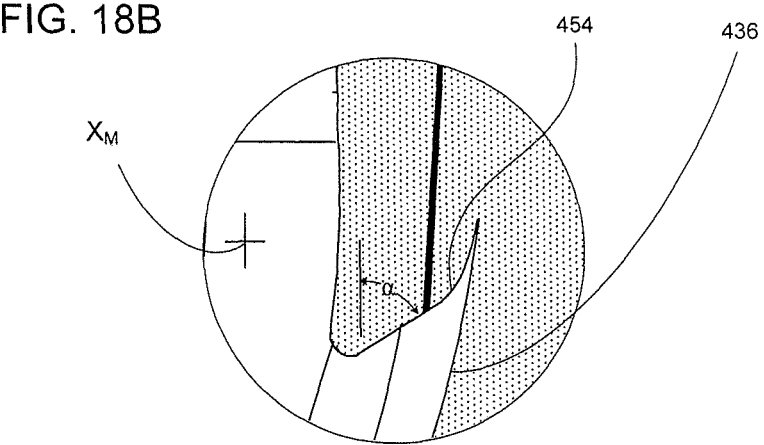
Figure 19A:
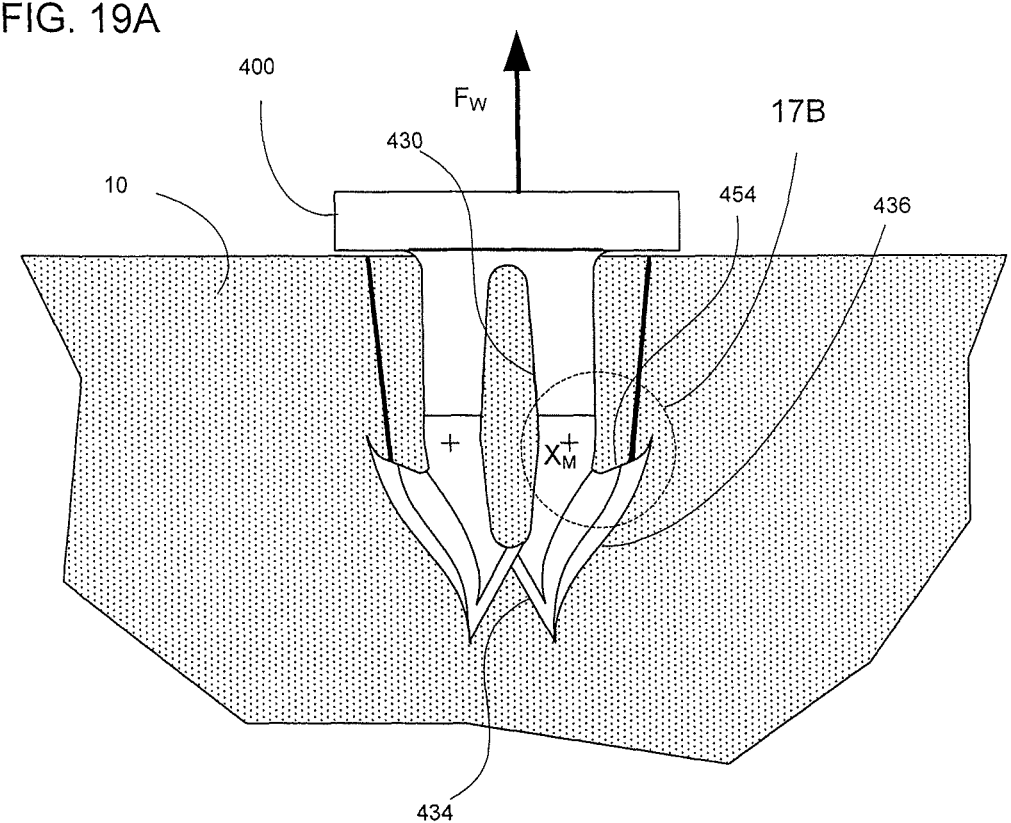
FIGS. 19A and 19B are section views illustrating an inserted fastener according to an embodiment of the invention in a deformed configuration produced by a withdrawal force.
Figure 19B:
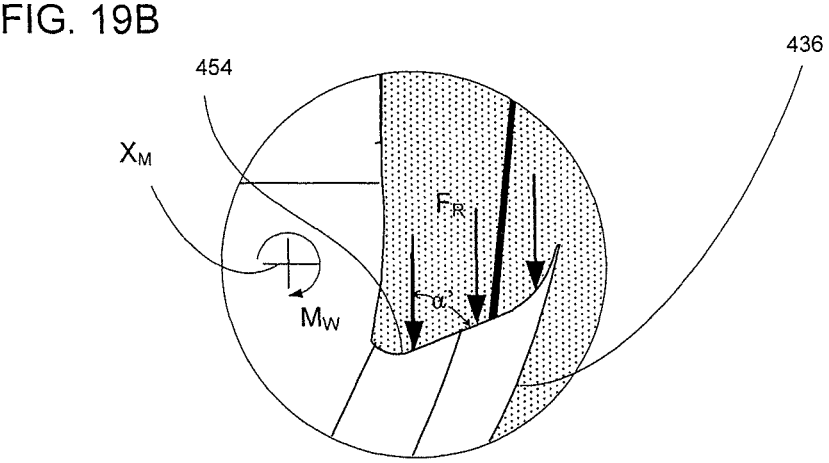

With reference to FIGS. 18 and 19, an exemplary fastener 400 with features similar to those of the fastener 200 of FIGS. 8 and 9 will be used to illustrate this feature. The exemplary fastener 400 is a dual leg fastener with an inner barb 434 and an outer barbs 436 on each leg 430. It can be seen that once the fastener 400 has been inserted, application of a withdrawal force will produce resistance forces applied by the tissue 10 to the anchoring element 432 of each leg 430. A primary surface upon which these resistance forces will act is the distal surface 454 of the outer barb 436. As shown in FIG. 18B, the distal surface 454 presents an angle α with respect to an axis parallel to the longitudinal axis of the fastener. In the unstressed exemplary fastener 400, this undeflected angle is approximately 60 degrees. The barbs 434 and 436 are configured so that the net resistance force applied to the anchoring element causes a moment $M_W$ about a point $X_M$ near the distal end of the leg stem supporting the anchoring element. The leg stem is configured so that if the withdrawal force $F_W$ is large enough, this moment will cause the material near the point $X_M$ to yield, thereby allowing the anchoring element to pivot to the deflected position shown in FIGS. 19A and 19B. The result of this pivoting action is that the distal surface 454 presents a surface that is more normal to the direction of the resistance force, thus increasing the effective surface over which the resistance forces act. This is illustrated in FIG. 19B by the angle α', which is greater than the pre-deformation angle α, indicating that the distal surface 454 is "flatter" relative to the direction of the withdrawal force and the opposing resistance forces. In the illustrated embodiment, the angle α' is approximately 70 degrees, indicating an angle change of 10 degrees due to the moment $M_W$ and consequent rotational deformation. This angle change results in a significant increase in the resistance force acting on the anchoring element, and thus, the amount of force required to remove the fastener 400.

It will be understood that, depending on the configuration, the rotation of the anchoring element of each leg will also change the angle of the distal surface of the inner barb 434. Like the outer barb 436, the inner barb 434 may be configured to increase the withdrawal resistance force when the anchoring element pivots in response to the applied withdrawal force.

The withdrawal force $F_Y$ at which the anchoring element of a typical fastener 400 begins to rotationally deform can be estimated by the following equation:

$$F_Y = (2ya^2\sigma_Y)/x \qquad \text{Eq 4:}$$

where $\sigma_Y$ is the yield bending stress, a is the square dimension of the leg stem cross section at its weakest point adjacent the distal end of the stem, and x is the effective moment arm over which the net resistive force acts (i.e., the distance from point $X_M$.) For a typical fastener having a leg formed from an 85/15 blend of PLA/PGA, the yield stress $\sigma_Y$ will be approximately 8000 psi. For a square dimension of 0.022 and an effective moment arm of 0.058, the critical withdrawal load $F_Y$ is estimated to be on the order of 1.34 lbs.

The fastener material and geometry may be designed such that bending of the anchoring element occurs at relatively low pull-out forces or very low tensile loads. Further, the fastener may be designed such that this deformation occurs when the fastener is loaded in shear such as may be experienced when the fastener is subjected to "rocking" or being pulled through the tissue off-angle.

It will be understood that configuration of the anchoring element to deform in response to a withdrawal force as described above is not limited to fasteners configured to deform upon insertion as previously described herein. It will also be understood, however, that this approach is particularly effective for fasteners that use post-insertion lateral deflection to laterally embed a portion of the anchoring element beneath uncut tissue.

Many embodiments and adaptations of the present invention, other than those herein described with reference to the exemplary embodiments, will be apparent to those skilled in the art by the foregoing description, without departing from the substance or scope of the invention. While the present invention has been described herein in detail in relation to its exemplary embodiments, it is to be understood that this disclosure is only illustrative and exemplary of the present invention. Accordingly, the foregoing disclosure is not intended to be construed so as to limit the present invention or otherwise to exclude any other such embodiments, adaptations, variations, modifications, and equivalent arrangements. The claimed invention is limited only by the following claims.

What is claimed is:

1. A fastener for penetrating body tissue upon application of a distally-directed insertion force, the fastener comprising:
    a head having a proximal head surface and a distal head surface, at least a portion of the distal head surface being configured for bearing on a surface of the body tissue or a material to be attached to a surface of the body tissue, the head defining a longitudinal axis extending through the proximal and distal head surfaces;

a passage extending between the proximal head surface and the distal head surface, the passage being configured to receive an elongated member of an applicator, whereby to temporarily secure a plurality of fasteners in axially-stacked disposition within the applicator and to index a plurality of the fasteners for serial deployment by the applicator; and a plurality of legs extending distally from the distal head surface, each leg comprising a resilient shaft having a proximal end attached to the distal head surface and a pointed distal end including an inclined edge;

wherein the shaft of each leg is resiliently biased outwardly relative to the longitudinal axis in a pre-insertion configuration;

and further wherein (i) the inclined edges of the pointed distal ends of the plurality of legs are configured so that when the fastener is being driven into tissue, the direct engagement of the inclined edges with the tissue generates a lateral force on the legs so that the legs are resiliently deflected inwardly toward the longitudinal axis, and (ii) when the fastener is no longer being driven into tissue, the outward bias of the plurality of legs causes the legs to resiliently return toward the pre-insertion configuration and securely anchor the fastener in the tissue.

2. A fastener according to claim 1 wherein the lateral force is a function of at least one of (i) a longitudinal force applied to the head of the fastener during penetration, and (ii) a longitudinal velocity of the fastener during penetration.

3. A fastener according to claim 1 wherein each of the plurality of legs further comprises an anchoring element for penetrating into the body tissue when the fastener is no longer being driven into the tissue.

4. A fastener according to claim 3 wherein each leg has an inner lateral surface and an outer lateral surface, at least a portion of the inner lateral surface and the outer lateral surface being defined by the shaft of the leg.

5. A fastener according to claim 4 wherein the anchoring element comprises an outer barb extending in an outward direction, the outer barb being disposed at the proximal end of the inclined edge of the pointed distal end.

6. A fastener according to claim 5 wherein the outer barb is configured to penetrate laterally into the body tissue when the leg is biased toward the pre-insertion configuration.

7. A fastener according to claim 5 wherein the inclined edge of the pointed distal end has a concave profile.

8. A fastener according to claim 5 wherein the first tapered leading edge has a reflexive curve profile when viewed along a line perpendicular to a plane through the leading edge and the longitudinal axis, the reflexive curve being convex adjacent the distal barb point and concave adjacent the first proximal barb point.

9. A fastener according to claim 5 wherein each anchoring element comprises an inner barb extending in the inward direction.

10. A fastener according to claim 4 wherein the inner lateral surface of the shaft of each leg is set at an angle of 0 to about 10 degrees with respect to the longitudinal axis.

11. A fastener according to claim 4 wherein the shaft of each leg is tapered such that a lateral cross-sectional area at the distal end of the leg is smaller than a lateral cross-sectional area at the proximal end of the shaft.

12. A fastener according to claim 4 wherein a first leg of the plurality of legs and a second leg of the plurality legs are positioned in opposition so that the inner lateral surface of the first leg faces the inner lateral surface of the second leg and so that when the lateral force on each leg exceeds the predetermined level, the deflected portions of the first and second legs are deflected toward one another.

13. A fastener according to claim 1 wherein the legs are formed from a thermoplastic material.

14. A fastener according to claim 1 wherein the head and legs are formed as a single integral body.

15. A fastener according to claim 14 wherein the single integral body comprises a bioabsorbable material.

16. A fastener according to claim 15 wherein the bioabsorbable material is selected from the group consisting of homopolymers and copolymers of lactide, glycolide, polyglycolide, and polylactide.

17. A fastener according to claim 15 wherein the bioabsorbable material is a blend of polylactic acid (PLA) and polyglycolic acid (PGA) in a ratio in a range of 65/35 PLA/PGA to 95/5 PLA/PGA.

18. A fastener according to claim 16 wherein a blend ratio is 85/15 PLA/PGA.

19. A fastener according to claim 1 wherein the inclined edge of the pointed distal end of the shaft of each leg comprises a distal end and a proximal end, and further wherein the distal end of the inclined edge is disposed closer to the longitudinal axis than the proximal end of the inclined edge, such that the inclined edge is tapered outwardly in the distal-to-proximal direction.

20. A fastener according to claim 19 wherein the proximal end of the inclined edge is spaced from the shaft of the leg so as to form a barb at the proximal end of the inclined edge.

21. A method of applying a fastener to a body tissue, comprising:

providing a fastener for penetrating body tissue upon application of a distally-directed insertion force, the fastener comprising:

a head having a proximal head surface and a distal head surface, at least a portion of the distal head surface being configured for bearing on a surface of the body tissue or a material to be attached to a surface of the body tissue, the head defining a longitudinal axis extending through the proximal and distal head surfaces;

a passage extending between the proximal head surface and the distal head surface, the passage being configured to receive an elongated member of an applicator, whereby to temporarily secure a plurality of fasteners in axially-stacked disposition within the applicator and to index a plurality of the fasteners for serial deployment by the applicator; and a plurality of legs extending distally from the distal head surface, each leg comprising a resilient shaft having a proximal end attached to the distal head surface and a pointed distal end including an inclined edge;

wherein the shaft of each leg is resiliently biased outwardly relative to the longitudinal axis in a pre-insertion configuration;

and further wherein (i) the inclined edges of the pointed distal ends of the plurality of legs are configured so that when the fastener is being driven into tissue, the direct engagement of the inclined edges with the tissue generates a lateral force on the legs so that the legs are resiliently deflected inwardly toward the longitudinal axis, and (ii) when the fastener is no longer being driven into tissue, the outward bias of the plurality of legs causes the legs to resiliently return toward the pre-insertion configuration and securely anchor the fastener in the tissue;

imparting a longitudinal insertion force to the fastener sufficient to cause the inclined edges of the pointed distal ends of the plurality of legs to penetrate the body tissue and to generate a lateral force on the legs so that the legs are resiliently to deflected inwardly toward the longitudinal axis; and removing the longitudinal insertion force previously imparted to the fastener so as to allow the plurality of legs to resiliently return toward the pre-insertion configuration and securely anchor the fastener in the tissue.

22. A method according to claim 21 further comprising:
compressing the body tissue prior to imparting the longitudinal insertion force to the fastener.

23. A method according to claim 21 wherein the longitudinal insertion force imparts an impulse to the fastener in a range of 25 to 100 lb-sec.

24. A method according to claim 21 further comprising:
positioning a repair material intermediate the fastener and the body tissue prior to imparting the longitudinal insertion force to the fastener.

* * * * *